US006936113B2

(12) United States Patent
Pohl

(10) Patent No.: US 6,936,113 B2
(45) Date of Patent: Aug. 30, 2005

(54) METHOD FOR REMOVING POLYMER FILMS IN THE MANUFACTURE OF AQUEOUS COMPOSITIONS CONTAINING ACRYLATES COPOLYMER

(75) Inventor: Stanley Pohl, Scarsdale, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 169 days.

(21) Appl. No.: 10/080,459

(22) Filed: Feb. 22, 2002

(65) Prior Publication Data

US 2002/0183221 A1 Dec. 5, 2002

Related U.S. Application Data

(60) Provisional application No. 60/271,812, filed on Feb. 27, 2001.

(51) Int. Cl.$^7$ ................................................ B08B 7/04
(52) U.S. Cl. ............................ 134/28; 134/3; 134/29; 134/38; 510/201; 510/469
(58) Field of Search ............................... 134/2, 3, 4, 38, 134/39, 40, 42; 510/180, 181, 201, 202, 245, 254, 370, 372, 376, 469; 8/405, 406, 649

(56) References Cited

U.S. PATENT DOCUMENTS

| | | | |
|---|---|---|---|
| 3,816,321 A | 6/1974 | Kleinschmidt | |
| 4,776,855 A | 10/1988 | Pohl et al. | |
| RE33,786 E | 1/1992 | Pohl et al. | |
| 5,376,146 A | 12/1994 | Casperson et al. | |
| 5,393,305 A | 2/1995 | Cohen et al. | |
| 5,597,789 A | 1/1997 | Sadlowski | |
| 5,817,614 A | 10/1998 | Miracle et al. | |
| 5,976,195 A | 11/1999 | De La Mettrie et al. | |
| 5,981,456 A | 11/1999 | Tartakovsky et al. | |
| 6,004,355 A | 12/1999 | Dias et al. | |
| 6,022,381 A * | 2/2000 | Dias et al. | 8/406 |
| 6,074,439 A | 6/2000 | De La Mettrie et al. | |
| 6,309,426 B1 * | 10/2001 | Dias et al. | 8/407 |
| 6,398,821 B1 * | 6/2002 | Dias et al. | 8/406 |
| 6,432,147 B1 * | 8/2002 | Dias et al. | 8/408 |

FOREIGN PATENT DOCUMENTS

WO    WO 98/27945    *    6/1998

* cited by examiner

*Primary Examiner*—Alexander Markoff
(74) *Attorney, Agent, or Firm*—Brian M. Bolam; Michael J. Sambrook; Tara M. Rosnell

(57) ABSTRACT

This invention relates to a method to facilitate the removal of adherent polymeric films from a hard surface occasioned by the evaporation of solvent from compositions containing an anionic acrylates copolymer, the method comprising incorporating a phosphate ester surfactant into the compositions, and washing the film from the surface to which it adheres.

14 Claims, No Drawings

US 6,936,113 B2

METHOD FOR REMOVING POLYMER FILMS IN THE MANUFACTURE OF AQUEOUS COMPOSITIONS CONTAINING ACRYLATES COPOLYMER

This application claims the benefit of Provisional application Ser. No. 60/271,812, filed Feb. 27, 2001.

FIELD OF THE INVENTION

This invention relates to a method to facilitate the removal of adherent polymeric films from a hard surface occasioned by the evaporation of solvent from compositions containing an acrylates copolymer, the method comprising incorporating a phosphate ester surfactant into the compositions, and washing the film from the surface to which it adheres. In particular, the invention relates to compositions containing an oxidizing agent; an acrylates copolymer, and one or more phosphate ester surfactants, wherein said compositions are manufactured using stainless steel equipment.

BACKGROUND OF THE INVENTION

Oxidation dye precursors are colorless compounds that undergo oxidative coupling in the presence of hydrogen peroxide to form colored molecules in the cortex of the fiber. Such precursors, namely, primary intermediates and couplers, form the basis of cosmetic products for permanently coloring hair.

In practice, oxidation hair dye products comprise two parts—a hair dye composition containing the dye precursors in a solvent system, and a developer composition that comprises an oxidizing agent, especially hydrogen peroxide. The first and second parts are mixed immediately before application to the hair, at which time the precursors are able to oxidatively couple owing to the presence of the oxidizing agent.

The final mixture as it is applied to the hair should be a thickened liquid, preferably with a thixotropic viscosity, so that it stays put on the hair and does not run or drip during the period of application. Many different thickening systems have been used for this purpose. One class of thickening agents used for this purpose is acrylates copolymers, an anionic polymer sold, e.g., under the tradename Aculyn 33 which can be included in the acidic hydrogen peroxide developer composition. (Acrylates copolymer is the chemical designation used for acrylic acid/methacrylic acid copolymers by the International Cosmetic Ingredient Dictionary.) At an acidic pH, the anionic acrylates copolymer is in its acidic form and the peroxide developer composition is a thin free flowing liquid. When the hair dye and peroxide developer compositions are mixed, the pH of the mixture is alkaline, the polymer is neutralized, and thickening is provided.

A number of patents have been issued covering the use of polymers for thickening oxidation dyes, including the following: U.S. Pat. No. 4,776,855; U.S. Pat. No. 5,393,305; U.S. Pat. No. 5,376,146; U.S. Pat. No. 5,976,195; U.S. Pat. No. 5,988,295; U.S. Pat. No. 6,074,439; and U.S. Pat. No. RE 33,786 the foregoing patents being incorporated herein by reference thereto.

This method of thickening oxidative hair dye product compositions, i.e., the composition comprising a mixture of the first part hair dye composition and the second part developer composition, is advantageous because the individual first part hair dye composition and second part developer composition can each be highly aqueous, i.e., neither requires a high viscosity or specialized rheology. Accordingly, the resulting highly aqueous, thickened hair dye product composition is characterized by having high dyeing efficiency.

Disadvantageously, the anionic acrylates copolymer of the present invention tends to form an adherent polymeric film on the equipment (e.g., mixing tanks, storage tanks, etc.) used in manufacturing, which is difficult to remove, requiring extensive cleanup procedures. For example, the use of a hot alkali solution has been used with some success. This is a particularly vexing problem when stainless steel vessels are used for formulating, e.g., hydrogen peroxide compositions, because scrubbing such vessels can scratch the surface of the vessel, requiring that the vessel be repassivated before further use.

Developer compositions are known that contain various surfactants, e.g., polyethoxylated alcohols and phenols, such as ceteareth-20 and nonoxynol-4, and anionic surfactants such as sulfated castor oil. Even when such surfactants are present in the anionic acrylates copolymer-containing composition, the polymers tend to form adherent polymeric films and cleaning of the manufacturing vessels is a serious problem.

SUMMARY OF THE INVENTION

In accordance with the present invention, a method is provided to facilitate the cleaning of hard surfaces, e.g., glass and metal, contacted by an anionic acrylates copolymer during the manufacture of compositions containing such polymer and onto which a polymeric film had formed. Film formation occurs during the manufacture of such compositions in which the anionic acrylates copolymer is incorporated when the solvent, typically water or a water-soluble organic solvent mixture, has evaporated, leaving a polymer residue that adheres to the surface. Because the compositions being manufactured invariably require mixing, a solution or dispersion of the polymer will come into contact with the walls of mixing vessels, and a film of the polymer is often formed before the vessel can be cleaned. Similarly, piping, agitators, storage tanks, pumps and other equipment commonly found in chemical manufacturing plants come into contact with the polymer while dissolved or dispersed, following which the solvent evaporates leaving a residual polymeric film. Moreover, spills as may occur during use of the polymer-containing composition, e.g., when a polymer solution is sloppily transferred to a vessel through a manhole, result in polymeric films on exterior surfaces and on platforms, etc. This also may occur during the manufacture of the anionic acrylates copolymer itself, especially during storage of aqueous solutions or dispersions of the anionic polymer prior to sale.

We have found that, surprisingly, there is a markedly reduced tendency for the anionic acrylates copolymers to form adherent polymeric films on surfaces coming into contact with the polymer solutions and dispersions when a phosphate ester surfactant is present in the solution or dispersion.

The anionic acrylates copolymer may be homopolymers or copolymers, and may be linear, nonlinear or cross-linked.

The phosphate ester surfactant has the general structure

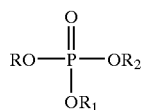

wherein R, $R^1$ and $R^2$ may be hydrogen, an alkyl of from 1 to about 22 carbons, preferably from about 12 to 18 carbons, or an alkoxylated alkyl of from 1 to about 22 carbons, preferably from about 12 to 18 carbons, and having 1 or more, preferably from about 2 to about 25, most preferably 2 to 12, moles ethylene oxide, with the proviso that at least one of R, $R^1$ and $R^2$ is an alkyl or alkoxylated alkyl as previously defined but having at least 6 alkyl carbons in said alkyl or alkoxylated alkyl group.

In accordance with the present invention, there is provided a method of cleaning surfaces, especially metal surfaces, in particular tanks, piping, agitators, pumps, and the like, used in the manufacture, transport and storage of acrylates copolymer-containing compositions, in particular aqueous compositions, onto which said polymer has formed an adherent film, comprising incorporating a phosphate ester surfactant in said compositions, and washing the surface to substantially remove the polymeric film.

In another aspect of the present invention, aqueous compositions are provided in which an acrylates copolymer[1] is used as a thickening agent, the aqueous compositions further comprising a phosphoric acid ester surfactant, whereby an adherent film of the polymer occasioned by the evaporative drying of the composition onto a hard surface is more easily removed from said surface. Accordingly, suitable compositions comprise acrylates copolymer; the phosphate ester surfactant, and water. In particular the presence of the phosphoric acid ester surfactant facilitates the removal of the composition from metal, most especially, stainless steel surfaces.

[1]Nomenclature of the International Cosmetic Ingredient Dictionary

The present invention is most advantageous when stainless steel is used as the material of construction for the processing equipment in facilities manufacturing acrylates copolymer-containing compositions. This is because the aggressive removal of a difficult-to-remove film of acrylates copolymer may damage the stainless steel surface of equipment, especially mixing tanks. Such damage might require repassivization of the surface. Accordingly, incorporation of the phosphate ester surfactant in acrylates copolymer-containing compositions to facilitate removal of any polymeric film formed during or after process manufacture of the composition would reduce the tendency to damage the stainless steel surface.

Such benefit is important in the manufacture of any product composition containing the film forming acrylates copolymer and especially where stainless steel is employed. One such instance is in the manufacture of oxidative hair dye products that comprise a hair dye composition of the oxidation dye precursors and a developer composition that contains an oxidizing agent, most typically hydrogen peroxide. The manufacture of the developer composition may incorporate acrylates copolymer where stainless steel is the construction material of choice for hydrogen peroxide and many other oxidizing agents.

The present invention further concerns compositions containing a film forming acrylates copolymer as a solution or dispersion in an appropriate solvent. In particular the present invention is drawn to such compositions containing acrylates copolymer as a non-associative-type thickening agent for oxidation hair dye products, the copolymer being present in the developer composition of that product.

DETAILED DESCRIPTION OF THE INVENTION

The present invention concerns a method of cleaning hard surfaces such as glass or metal, in particular metal surfaces, and especially stainless steel surfaces, onto which has formed a polymeric film of acrylates copolymer occasioned by evaporation of the solvent in which the polymer is dissolved or dispersed. According to the present invention, the incorporation of a phosphate ester surfactant during manufacture of the composition facilitates removal of the film.

In particular the method of the present invention concerns the cleaning of stainless steel surfaces, which can become damaged during vigorous cleaning, which would then require the surface to be repassivated.

The Anionic Acrylates Copolymers

Acrylates copolymer, which is the chemical designation used by The International Cosmetic Ingredient Dictionary and Handbook (Eighth Edition, 2000), incorporated herein by reference, is a copolymer of acrylic acid, methacrylic acid or one of their simple esters, and may be the alkali metal or ammonium salts of such copolymers. Illustrative of acrylates copolymers are Aculyn 33, sold by Rohm and Haas; Capigel 98 sold by Seppic; Luvimer30E sold by BASF; and Salcare SC8, sold by Allied Colloids.

In a preferred embodiment of the invention, the compositions of the present invention are polymer thickened, acidic developer compositions containing an oxidizing agent for use in oxidation hair dye products. In acidic compositions of course, the polymer salts would not be employed.

As used herein, the term "hair dye composition" refers to the composition containing primary intermediate and coupler oxidation dyes prior to admixture with the developer composition. The term "developer composition" refers to compositions containing an oxidizing agent, especially hydrogen peroxide, prior to admixture with the hair dyeing composition. The term "hair dye product" or "hair dye system" interchangeably refers to the combination of the hair dyeing composition and the developer composition before admixture, and may further include a conditioner product and instructions, such product or system often being provided packaged as a kit. The term "hair dye product composition" refers to the composition formed by mixing the hair dye composition and the developer composition.

Acrylates copolymer used as a thickening agent in such oxidative hair dye products is incorporated in the developer composition, which has an acidic pH. At the acidic pH, the polymer is dissolved or dispersed in the solvent, while at alkaline pH the polymer thickens the composition. This occurs when the developer composition is mixed with the alkaline hair dye composition to form the hair dye product composition. Aculyn 33 from Rohm and Haas is preferred for this purpose. See Technical Brochure FC-310a, Aculyn Thickeners and Stabilizers For Personal Care, Rohm and Haas (May 1996) incorporated by reference.

The Phosphate Ester Surfactant

The second essential component of the compositions of the present invention is the phosphate ester surfactant. By incorporating the phosphate ester surfactant into compositions containing the acrylates copolymer, it has been found that films of the polymer formed on a hard surface when the solvent has evaporated are more easily removed.

Phosphate esters suitable for incorporation into the compositions of the present invention have the formula The phosphate ester surfactant has the general structure

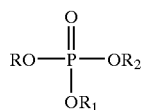

wherein R, $R^1$ and $R^2$ may be hydrogen, an alkyl of from 1 to about 22 carbons, preferably from about 12 to 18 carbons, or an alkoxylated alkyl of from 1 to about 22 carbons, preferably from about 12 to 18 carbons, and having 1 or more, preferably from about 2 to about 25, most preferably 2 to 12, moles ethylene oxide, with the proviso that at least one of R, $R^1$ and $R^2$ is an alkyl or alkoxylated alkyl as previously defined but having at least 6 alkyl carbons in said alkyl or alkoxylated alkyl group.

Monoesters in which $R^1$ and $R^2$ are hydrogen and R is selected from alkyls of 10 to 18 carbons and alkoxylated fatty alcohols of 10 to 18 carbons and 2 to 12 moles ethylene oxide are preferred. Among the preferred phosphate ester surfactants, mention may be made of C 12–16 Pareth-6 Phosphate, C8–10 Alkyl Ethyl Phosphate, C9–15 Alkyl Phosphate, Ceteareth-2 Phosphate, Ceteareth-4 Phosphate, Ceteareth-5 Phosphate, Ceteareth-10 Phosphate, Ceteth-8 Phosphate, Ceteth-10 Phosphate, Cetyl Phosphate, C6–10 Pareth-4 Phosphate, C12–13 Pareth-10 Phosphate, C12–15 Pareth-2 Phosphate, C12–15 Pareth-3 Phosphate, C12–15 Pareth-6 Phosphate, C12–15 Pareth-8 Phosphate, C12–15 Pareth-10 Phosphate, C12–16 Pareth-6 Phosphate, DEA-Ceteareth-2 Phosphate, DEA-Cetyl Phosphate, DEA-Oleth-3 Phosphate, DEA-Oleth-5 Phosphate, DEA-Oleth-10 Phosphate, DEA-Oleth-20 Phosphate, Deceth-9 Phosphate, Deceth-4 Phosphate and Deceth-6 Phosphate.

The Solvent

The compositions of the present invention are aqueous, and may comprise water as the sole solvent, or may comprise water in combination with an essentially water-soluble organic solvent such as a mono- or polyhydric alcohol. The compositions contain a sufficient amount of solvent so that the polymer is dissolved in the composition, or is dispersed in the composition. Preferably, water is the major component of the solvent system. Preferably, the solvent constitutes from about 60 to about 93% of the composition on a weight basis, most preferably from about 70 to about 85% by weight.

Useful organic solvents are $C_1$ to $C_6$ alcohols and $C_2$ to $C_8$ polyols. Especially useful alcohols for use in the solvent system of the present invention are ethyl alcohol, isopropyl alcohol and butyl alcohol. Especially useful pohydric alcohols of the present invention are ethylene glycol, propylene glycol, hexylene glycol, and glycerin. The alcohols typically comprise from about 0 to about 25% by weight of the composition.

Preferred Compositions

The preferred compositions of the present invention contain hydrogen peroxide and are used as developer compositions in oxidative hair dye products.

The developer compositions comprise on a weight basis by weight of the composition: (a) from about 0.1 to about 10 of acrylates copolymer, preferably 0.2 to 5%, most preferably 0.5 to 2.5%; (b) from about 1 to about 15% hydrogen peroxide, preferably 3 to 12, most preferably 3 to 9; (c) from about 0.1 to about 15% of a phosphate ester surfactant, preferably 0.5 to 10, most preferably 0.5 to 5, and (d) solvent.

In the manufacture of the developer composition containing the hydrogen peroxide oxidizing agent, it is necessary to use stainless steel equipment, in particular stainless steel mixing tanks, to avoid corrosion caused by the hydrogen peroxide.

Moreover, there is a tendency for the developer composition, which has an acidic pH, typically a pH from about 2.5 to about 6.5, to foam during mixing, mixing being necessary to ensure homogeneity of the composition. As a consequence the side wall of the tank is coated with a thin layer of developer composition, which dries rapidly when mixing ends. The resulting polymeric film has proven to be quite difficult to remove and requires exposure to high pressure cleaning sprays, often with highly alkaline cleaning products. Such treatment can cause damage to the stainless steel surface of the mixing tank, requiring it to be repassivated. This is true even though developer compositions typically contain a nonionic surfactant such as nonoxynol-2, nonoxynol-4, $C_{11}$–$C_{15}$ Pareth-7, $C_{12}$–$C_{15}$ Pareth-9, and $C_{12}$–$C_{15}$ Pareth-3.

The incorporation of the phosphoric acid ester into the developer composition has been found effective to reduce the tenacity of the polymeric film to the side wall of the stainless steel.

The developer compositions contain any suitable oxidizing agent, particularly hydrogen peroxide and its addition compounds. Thus, suitable oxidizing agents include urea peroxide, the alkali metal and ammonium salts of persulfate, perborate and percarbamate, especially the sodium salt, and melamine peroxide. The oxidizing agent is preferably present as a 3 to 12% (10 to 40 volume), most especially 6%, aqueous hydrogen peroxide solution. See e.g., deNavarre, The Chemistry and Manufacture of Cosmetics, Vol. IV, p. 847–50, ($2^{nd}$ Edition, 1975).

The developer composition of the present invention may also contain, in addition to the anionic acrylates copolymer, hydrogen peroxide, the phosphate ester surfactant, and water, one or more additional ingredients.

Accordingly, the developer composition may contain an acidifying agent to provide an acid pH, preferably in the range of from about 3 to about 5.5, most preferably from about 3.5 to about 4.5. At this pH the developer composition preferably has an essentially Newtonian rheology, with a viscosity less than about 1000 cps, preferably less than about 500 cps, most preferably less than 100 cps. The preferred polymer thickening agent is Aculyn 33, a copolymer of two or more monomers of acrylic acid, methacrylic acid or one of their simple esters sold by Rohm and Haas. Neutralization by raising pH converts this polymeric thickener into a clear viscous solutions. Such thickening occurs when the developer is admixed with the alkaline hair dye composition to provide a hair dye product composition having a pH of from about 8 to about 11, preferably from about 9 to 10.5. Advantageously, the Aculyn 33 polymer is peroxide stable. Most preferably a mixture of an associative and non-associative polymer is employed. See U.S. Pat. No. 5,376,146.

The developer composition may also include a surfactant other than the phosphate ester surfactant, which surfactant is selected from the group consisting of anionic, nonionic, and amphoteric (including zwitterionic) surfactants. As used herein "surfactant" means a surfactant other than a cationic surfactant or a phosphate ester surfactant.

(Cationic surfactants, generally included as hair conditioning materials, are considered separately below.) Suitable surfactants, other than cationic surfactants, include fatty alcohol sulfates, ethoxylated fatty alcohol sulfates, alkylsulfonates, alkylbenzensulfonates, alkyltrimethylammonium salts, alkylbetaines, ethoxylated fatty alcohols, ethoxylated fatty acids, ethoxylated alkylphenols, block polymers of ethylene and/or propylene glycol, glycerol esters, phosphate esters, fatty acid alkanol amides and ethoxylated fatty acid esters, alkyl sulfates, ethoxylated alkyl sulfates, alkyl glyceryl ether sulfonates, methyl acyl taurates, acyl isethionates, alkyl ethoxy carboxylates, fatty acid mono- and diethanolamides.

The amount of surfactants in the developer compositions is normally from about 0.1% to 30% by weight, preferably 1% to 15% by weight.

The developer composition may also include a conditioning agent. Materials suitable as conditioning agents include silicones and silicone derivatives; hydrocarbon oils; cationic surfactants that are monomeric quaternary compounds, and quaternized polymers. Monomeric quaternary compounds are typically cationic compounds, but may also include betaines and other amphoteric and zwitterionic materials that provide a conditioning effect. Suitable monomeric quaternary compounds include behentrimonium chloride, stearalkonium chloride, and many other compounds. See WO 98/27941 incorporated by reference. Quaternized polymers are typically cationic polymers, but may also include amphoteric and zwitterionic polymers. Useful polymers are exemplified by polyquaternium-4, polyquaternium-6, polyquaternium-7, polyquaternium-8, polyquaternium-9, polyquaternium-10, polyquaternium-22, polyquaternium-32, polyquaternium-39, polyquaternium-44 and polyquaternium-47. Silicones suitable to condition hair are dimethicone, amodimethicone, dimethicone copolyol and dimethiconol. See also WO 99/34770 published Jul. 15,1999, incorporated by reference, for suitable silicones. Suitable hydrocarbon oils would include mineral oil.

Conditioners are usually present in the hair developer composition in an amount of from about 0.01 to about 5% by weight of the hair dye composition.

Other optional ingredients include chelating and sequestering agents such as EDTA, dispersing agents, penetrating agents, etc., in concentrations effective to achieve their functional purpose.

Method of Cleaning Hard Surface

The polymeric films that are formed when the anionic amphiphilic film-forming polymer-containing compositions of the present invention evaporate are removed by washing the surface with a cleaning composition. As used herein cleaning composition may include water as a medium to rinse the surface, but preferably is an aqueous solution of a cleaning active. Cleaning actives may include alkali materials such as sodium hydroxide, potassium hydroxide, ammonium hydroxide, (not preferred because of odor), mono-, di- and triethanolamines; anionic, nonionic and amphoteric surfactants, including the phosphate ester of the present invention, and compatible mixtures thereof. Preferably, the pH of the cleaning composition will be alkaline or neutral, most especially alkaline with a pH of from about 8 to about 10. A particularly useful cleaner is DuBois T-Off, a commercially available caustic-containing cleaner, in a 5 to 15%, preferably 10% aqueous solution. The DuBois T-Off solution preferably is used at elevated temperature, especially from about 45 to 65° C. Preferably, the cleaning composition is sprayed under a moderate pressure of from about 15 to about 65 psig, most preferably from about 20 to about 40 psig, until the film is removed. The cleaning time varies depending upon the nature of the cleaning solution, the temperature of cleaning, the time between cleanings, and the age of the film. Generally, the wash time is from one to several minutes to two hours in the case of a long-term film build-up. Usually, the film is removed substantially, e.g., 90% or more of the film, in less than one hour. The application of the cleaning composition may be accompanied by scrubbing with a broom, brush or other device. Scrubbing is not preferred where the surface being cleaned is stainless steel.

The present invention is illustrated by the following examples. In this application the percentages are by weight of the total composition unless other wise indicated.

EXAMPLES 1 and 2

Examples of two developer compositions containing 6.15% hydrogen peroxide (approximately 20 volume $H_2O_2$); an anionic acrylates copolymer thickening agent, sufficient acidifying agent to provide a pH of 2.5–5, and varying concentrations of the phosphate ester surfactant laureth-4 phosphate are set forth in Table 1 below.

TABLE 1

Developer compositions containing acrylate copolymers and phosphate ester

| Ingredients | Example 1 | Example 2 |
|---|---|---|
| Water | QS to 100 | QS to 100 |
| Editronic acid | 0.08 | 0.08 |
| Disodium EDTA | 0.04 | 0.04 |
| Aculyn22/33[23] (20/80 mixture) | 5.0 | 4.0 |
| Trilaureth-4 phosphate | 2.5 | 4.0 |
| Hydrogen peroxide (50%) | 12.3 | 12.3 |

[2]Aculyn 22 is a 30% active polymer dispersion, and Aculyn is a 28% active polymer dispersion.
[3]Concentration is on an "as received" basis.

The benefits of having the phosphate ester surfactant in such developers containing anionic acrylates copolymers is demonstrated by the following experiments to simulate the adhesion and removal of polymer films on a metal surface. An amount (0.5 g) of developer solution is spread evenly over a stainless plate (7 cm by 2 cm), and allowed to dry overnight at room temperature to form a thick polymer residue. A thin polymer residue is produced when 0.2 g of developer solution is used. The polymer residue is then rinsed under tap water (30° C.) at a flow rate of 2 liters/minute. Rinsing continues until the polymer film is removed completely from the plate. The time it takes to do so (or the rinse time) is recorded, and the rinse times for different developer compositions are shown in Table 2 below. The polymer residues from the composition without phosphate ester takes more than 120 seconds to be removed. When formulated with phosphate ester, the films are removed in much shorter time, ranging from about 2 seconds to less than 30 seconds.

TABLE 2

Effect of added phosphate on rinse time

| Developer compositions | Rinse time for thick film | Rinse time for thin film |
|---|---|---|
| A. With 5% Aculyn 22/Aculyn 33 in water (Example 1 less phosphate) | >120 sec | >120 sec |
| B. With 5% Aculyn 22/Aculyn 33 in water plus 2.5% trilaureth-4 phosphate (Example 1) | 27 sec | 2.5 sec |

While the invention has been illustrated in connection with oxidative hair dyeing developer formulation, the invention is applicable to any type of formulations in which anionic acrylates copolymers are employed and there is a possible problem with the formation of undesirable film residues.

I claim:

1. A method of cleaning a surface on to which a polymeric film of acrylates copolymer has formed upon evaporation of solvent from an aqueous composition containing said polymer, the method comprising:
   (a) incorporating in said aqueous composition during its preparation from about 0.5% to about 5% by weight of said aqueous composition of a phosphate ester surfactant, and
   (b) washing the surface with a cleaning composition to substantially remove said polymeric film.

2. The method of claim 1 in which the surface is selected from the group consisting of glass and metal.

3. The method of claim 2 wherein the surface is metal.

4. The method of claim 3 wherein the surface is steel.

5. The method of claim 4 wherein the surface is stainless steel.

6. The method of claim 5 in which the composition comprises hydrogen peroxide and has an acidic pH.

7. A method of cleaning a stainless steel surface used in the manufacture, transfer and storage of an aqueous acidic composition containing acrylates copolymer and an oxidizing agent and to which surface said polymer has formed an adherent film, the method comprising
   (a) incorporating in said aqueous acidic composition during its preparation from about 0.5% to about 5% by weight of said aqueous acidic composition of a phosphate ester surfactant of the formula I

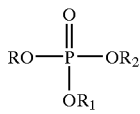

wherein R, $R^1$ and $R^2$ are each independently selected from the group consisting of hydrogen, an alkyl of from 1 to about 22 carbons, and an alkoxylated alkyl of from 1 to about 22 carbons and having from about 1 to about 25 moles ethylene oxide, with the proviso that at least one of R, $R^1$ and $R^2$ is an alkyl or alkoxylated alkyl as previously defined but having at least 6 alkyl carbons in said alkyl or alkoxylated alkyl group, and
   (b) washing the stainless steel surface with a cleaning composition to substantially remove said film.

8. The method of claim 7 wherein the oxidizing agent is hydrogen peroxide.

9. The method of claim 7 wherein the cleaning composition is an alkaline solution having a pH of from about 8 to about 10.

10. The method of claim 9 wherein the cleaning composition is applied under moderate pressure of from about 20 to about 40 psig.

11. A developer composition comprising on a weight basis by weight of the composition:
    (a) from about 6% to about 15% of a hydrogen peroxide oxidizing agent;
    (b) from about 0.5% to about 5% of a phosphate ester surfactant,
    (c) from about 0.1% to about 10% of acrylates copolymer; and
    (d) water,
wherein said developer composition has an acidic pH.

12. The composition of claim 11 wherein the pH is from about 2.5 to about 6.5.

13. The composition of claim 11 further comprising an organic cosolvent selected from the group consisting of $C_2$ to $C_6$ mono- and polyhydric alcohols.

14. The composition of claim 11 wherein the phosphate ester surfactant is selected from the group consisting of C12–16 Pareth-6 Phosphate, C8–10 Alkyl Ethyl Phosphate, C9–15 Alkyl Phosphate, Ceteareth-2 Phosphate, Ceteareth-4 Phosphate, Ceteareth-5 Phosphate, Ceteareth-10 Phosphate, Ceteth-8 Phosphate, Ceteth-10 Phosphate, Cetyl Phosphate, C6–10 Pareth-4 Phosphate, C12–13 Pareth-10 Phosphate, C12–15 Pareth-2 Phosphate, C12–15 Pareth-3 Phosphate, C12–15 Pareth-6 Phosphate, C12–15 Pareth-8 Phosphate, C12–15 Pareth-10 Phosphate, C12–16 Pareth-6 Phosphate, DEA-Ceteareth-2 Phosphate, DEA-Cetyl Phosphate, DEA-Oleth-3 Phosphate, DEA-Oleth-5 Phosphate, DEA-Oleth-10 Phosphate, DEA-Oleth-20 Phosphate, Deceth-9 Phosphate, Deceth-4 Phosphate and Deceth-6 Phosphate.

* * * * *